United States Patent [19]

Tarumi et al.

[11] Patent Number: 4,728,729

[45] Date of Patent: Mar. 1, 1988

[54] CYANOIMIDAZOLE NUCLEOSIDE DERIVATIVES

[75] Inventors: Yuzo Tarumi, Nishinomiya; Toshio Atsumi, Kawanishi; Masaru Fukui, Toyonaka, all of Japan

[73] Assignee: Sumitomo Pharmaceuticals Co., Ltd., Osaka, Japan

[21] Appl. No.: 709,647

[22] Filed: Mar. 8, 1985

[30] Foreign Application Priority Data

Mar. 14, 1984 [JP] Japan .................. 59-49563

[51] Int. Cl.[4] ................ C07H 19/067; C07H 19/052
[52] U.S. Cl. ............................ 536/23; 536/22
[58] Field of Search ............... 514/43, 49; 536/23

[56] References Cited

U.S. PATENT DOCUMENTS

| | | | |
|---|---|---|---|
| Re. 29,835 | 11/1978 | Witkowski et al. | 536/23 |
| 3,817,980 | 6/1974 | Vorbruggen et al. | 536/23 |
| 3,968,103 | 7/1976 | Robins et al. | 536/23 |
| 4,140,788 | 2/1979 | Atsumi et al. | 424/273 |
| 4,209,525 | 6/1980 | Atsumi et al. | 424/273 |
| 4,218,457 | 8/1980 | Atsumi et al. | 424/263 |
| 4,255,565 | 3/1981 | Marumoto et al. | 536/23 |
| 4,260,774 | 4/1981 | Atsumi et al. | 548/336 |
| 4,317,825 | 3/1982 | Atsumi et al. | 424/250 |
| 4,332,806 | 6/1982 | Atsumi et al. | 424/273 |
| 4,346,096 | 8/1982 | Sanjiki et al. | 424/273 |
| 4,410,696 | 10/1983 | Atsumi et al. | 542/427 |
| 4,464,531 | 8/1984 | Atsumi et al. | 536/17.4 |

FOREIGN PATENT DOCUMENTS

| | | | |
|---|---|---|---|
| 1078736 | 6/1980 | Canada | 536/23 |
| 0155164 | 9/1985 | European Pat. Off. | 514/43 |
| 100371 | 8/1979 | Japan | 536/23 |
| 0167515 | 9/1984 | Japan | 514/43 |

OTHER PUBLICATIONS

Sandler et al., Organic Functional Group Preparations, Academic Press, New York and London, 1968.
Journal of Antibiotics, 27, 775, (1974).
Journal of Heterocyclic Chemistry, 22, 529, (1984).
Journal of Heterocyclic Chemistry, 22, 849, (1984).

*Primary Examiner*—J. R. Brown
*Assistant Examiner*—Jenny Tou
*Attorney, Agent, or Firm*—Cushman, Darby & Cushman

[57] ABSTRACT

A novel cyanoimidazole nucleoside and derivative thereof, particularly 4-cyanoimidazolium-5-olate nucleoside and acyl derivatives thereof, and pharmaceutically acceptable salts thereof which are useful as antitumor agents and immunosuppressants, are prepared by dehydrating carboxamide derivatives of the formula:

wherein R is an acyl group, and then, if desired, deacylating.

8 Claims, No Drawings

CYANOIMIDAZOLE NUCLEOSIDE DERIVATIVES

The present invention relates to a novel cyanoimidazole nucleoside, its derivatives and pharmaceutically acceptable salts thereof, and also to preparation and use thereof. More particularly, the present invention pertains to 4-cyanoimidazolium-5-olate nucleoside, its acyl derivatives and pharmaceutically acceptable salts thereof useful as antitumor agents and immunosuppressants, a pharmaceutical composition containing at least one of them and a process for preparing them.

The novel cyanoimidazole nucleoside and its derivatives of the present invention are those represented by the following formula (I),

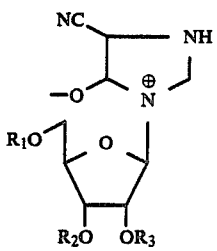

wherein $R_1$, $R_2$ and $R_3$ are each a hydrogen atom or an acyl group.

As used herein, the term an acyl group means an alkanoyl group having 1 to 4 carbon atoms, e.g. acetyl, n-propionyl, n-butyryl, iso-butyryl etc. or an aromatic acyl group such as aroyl group, e.g. benzoyl etc. So far, it has been known that bredinin or mizoribin, 4-carbamoyl-1-β-D-ribofuranosylimidazolium-5-olate, and its aglycone, 4-carbamoylimidazolium-5-olate, have immunosuppressive and antitumor activities (Kimio Mizuno et al, J. of Antibiotics, vol. 27 p. 775 (1974) and Canada Pat. No. 1,078,736).

We have carried out extensive studies of the related compounds of bredinin and its aglycone for the purpose of developing a new antitumor agent. As a result of this, we have found the cyanoimidazole nucleoside of the present invention possessing potent antitumor and immunosuppressive activities. Among various cyanoimidazole nucleosides represented by the formula (I), preferred is that wherein $R_1$, $R_2$ and $R_3$ are each a hydrogen atom.

The compounds of the formula (I) of the present invention can be easily prepared in a good yield by the following process.

The said cyanoimidazole nucleoside derivatives of the formula (I) wherein $R_1$, $R_2$ and $R_3$ are each an acyl group can be prepared by reacting a carboxamide derivative or carbamoylimidazole nucleoside of the formula (II):

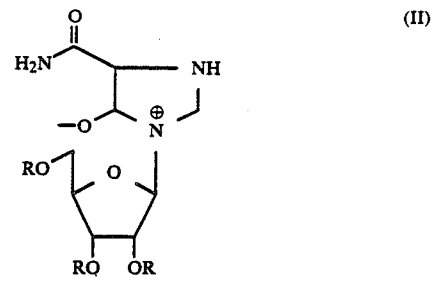

wherein R is an acyl group, with a dehydrating agent.

Examples of the dehydrating agent are triphenylphosphine, acetic anhydride, sulfurous oxychloride, toluenesulfonyl chloride, phosgene, benzenesulfonic acid, phosphorus pentoxide, phosphoryl chloride, aluminium chloride and dicyclohexylcarbodiimide. Preferably phosphoryl chloride can be used. A dehydrating agent can be used in an amount sufficient to complete the reaction, however, preferable amount of, for example, phosphoryl chloride may be usually about 2 molar equivalents to the carboxamide derivative (II).

The reaction can be carried out, usually in an inert solvent, by controlling the reaction temperature from 0° C. to room temperature, preferably at room temperature. The reaction can be completed in a few hours under room temperature. As the inert solvent, there may be used a hydrocarbon solvent, e.g. benzene, toluene, xylene, a halogenated hydrocarbon solvent, e.g. dichloromethane, chloroform, carbon tetrachloride, and the like. Acetonitrile can be used preferably.

After completion of the reaction, the desired compound (I) wherein $R_1$, $R_2$ and $R_3$ are each an acyl group can be obtained from the reaction mixture according to an ordinary method. For example, after the reaction mixture is neutralized and the solvent is removed in vacuo, the resulting residue is purified with column chromatography on reversed or normal phase silica gel.

The starting carbamoylimidazole nucleoside (II) can be prepared, for instance, by reacting 4-carbamoylimidazolium-5-olate of the formula:

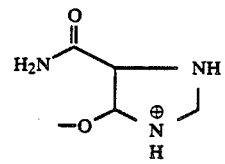

with a per-acylated ribofuranose derivative [Y. Tarumi et al., J. of Heterocyclic Chemistry vol. 22, p. 529 (1984)]. The cyanoimidazole nucleoside of the formula (I) wherein $R_1$, $R_2$ and $R_3$ are as defined above is, if desired, deprotected to give the corresponding fully or partially deprotected nucleosides. The deprotection is carried out by reacting the compound of the formula (I wherein $R_1$, $R_2$ and $R_3$ are each an acyl group with ammonia-methanol, or an alkali metal alkoxide in the presence of a solvent. Preferable alkali metal alkoxides are sodium methoxide, sodium ethoxide, potassium tert-butoxide and the like. While the solvent to be used is not limited in particular, alcohols such as methanol, ethanol, tert-butanol are preferable. Partial deprotection is carried out, for example, by treating the compound (I) with ammonia-methanol at a temperature of 0° to 5° C.

for a few hours to give 5'-monosubstituted product (I) wherein $R_1$ is alkanoyl group, $R_2$ and $R_3$ are each a hydrogen atom.

After completion of the reaction, the desired compound (I) wherein $R_1$, $R_2$ and $R_3$ are as defined above is obtained from the reaction mixture according to an ordinary method. For example, after the solvent is removed by distillation, the residue is purified by fractionation by column chromatography on reversed phase silica gel, or dissolved in water and the solution is neutralized by adding thereto cation exchange resin, e.g. Amberlite®IR-120, Dowex®50-X, 50W-X, etc. The resin is filtered off and the filtrate is concentrated in vacuo to give a residue, which is purified by column chromatography on reversed phase silica gel to give the desired product.

The salt of the compound (I) can be easily prepared by adding a base thereto. Typical examples of the base are an inorganic base, e.g., sodium hydroxide, potassium hydroxide, barium hydroxide, sodium bicarbonate, potassium bicarbonate, sodium carbonate, potassium carbonate, etc. and an organic base, e.g., pyridine, N,N-dimethylaniline, triethylamine, tri-n-butylamine, N-methylmorpholine, etc.

The compounds of the present invention possess potent antitumor activities against mouse experimental tumors such as Ehrlich carcinoma, Sarcoma 180, Lewis Lung Carcinoma, Colon 26, Colon 38, P-388 leukemia, L-1210 leukemia and the like, and growth inhibitory activities on various human tumor cells. The compounds of the formula (I) are useful as antitumor agents and they exhibit particularly excellent growth inhibitory activities against tumors and life prolongation effect. The antitumor activities of the compounds of the present invention were estimated according to the method described in "Cancer Research" vol. 43, p. 5851 (1983). The results are given in the following Table 1.

TABLE 1

| Compound | Dose (mg/kg/day) | Route | Schedule | Inhibition ratio (%) |
|---|---|---|---|---|
| 4-Cyano-1-β-D- | 80 | po | Days 1,5,9 | 99.8 |
| ribofuranosyl- | 40 | po | Days 1,5,9 | 99.8 |
| imidazolium- | 20 | po | Days 1,5,9 | 73.6 |
| 5-olate | 10 | po | Days 1,5,9 | 40.1 |

ICR/Jcl male mice, 5 weks old, were used, were used. Each test group was composed of 6 mice. Three million cells of Ehrlich carcinoma were injected in the hind leg. The drug was administered orally at days 1, 5, and 9. After sacrificing the mice at day 15, tumors were removed and weighed. The tumor growth inhibitory ratio was calculated according to the following formula.

$$\text{Inhibition ratio} = \left[1 - \frac{\text{The mean tumor weights of treated group}}{\text{The mean tumor weights of control group}}\right] \times 100$$

In vitro growth inhibition assay

In vitro growth inhibition activities were determined according to the method described in "Cancer Research", Vol. 43, p. 5851–5856 (1983).

In the case of suspension culture (lymphoma and leukemia cell lines), cells were cultured with various concentrations of the compound for 72 hr.

In the case of monolayer culture (solid tumor cell lines), cells were cultured for 24 hr without the compound in order to allow cells to attach on the culture plate. Then the culture medium was changed to a fresh medium containing various concentrations of the compound. Cells were further cultured for 72 hr to 120 hr, and then removed from the culture plate by 0.125% trypsin and 0.05% EDTA solution.

Cell numbers were counted with a Coulter Counter and $IC_{50}s$ were calculated.

The results are shown in Table 2.

TABLE 2

In vitro growth inhibitory activities of 4-cyano-1-β-D-ribofuranosylimidazolium-5-olate on various human tumor cell lines

| Cell line | Origin | IC50 (μM) |
|---|---|---|
| Lymphoma and Leukemia | | |
| HL-60 | promyelocytic leukemia | 0.87 |
| CCRF-HSB-2 | acute lymphoblastic leukemia | <3.0 |
| P3HR1 | Burkitt lymphoma | 4.6 |
| Solid tumor | | |
| QG-56 | lung squamous carcinoma | 2.8 |
| QG-90 | lung small cell carcinoma | 6.7 |
| A549 | lung cancer | 8.5 |
| Hela | uterine cervix cancer | 4.7 |
| KU-2 | renal cell carcinoma | 1.0 |
| DU 145 | prostate cancer | 4.4 |
| SCaBER | bladder squamous carcinoma | 5.0 |

As described in Table 2, 4-cyano-1-β-D-ribofuranosylimidazolium-5-olate possessed a potent growth inhibitory activities on various types of human tumor cell lines.

Immunosuppressive Activity

The immunosuppressive activity of the compound of the present invention was assayed in comparison with mizoribine which has been used in immunosuppressive therapy.

After a sheep red blood cell preparation (SRBC) was injected in mice, the compounds were administered orally once a day on day 0 to 3 and the plaque forming cell (PFC) number was measured on day 4 by Cunningham method. [Cunningham A. J. et al. Immunol. 14, 599(1968)].

As shown in Table 3, 4-cyano-1-β-D-ribofuranosylimidazolium-5-olate was more active than mizoribine and showed a potent activity in oral administration.

TABLE 3

Effect of 4-cyano-1-β-D-ribofuranosylimidazolium-5-olate and mizoribine on anti-SRBC PFC response in vivo.

| Compounds | Dose (mg/day p.o.) | PFC × 10⁻³/ spleen | Suppression (%) |
|---|---|---|---|
| 4-cyano-1-β-D- | 5 | 362 ± 123 | 0 |
| ribofuranosyl- | 25 | 4 ± 1 | 99 |
| imidazolium- | 50 | 0 | 100 |
| 5-olate | | | |
| Mizoribine | 5 | 496 ± 140 | 0 |
| | 25 | 113 ± 53 | 69 |
| | 50 | 39 ± 43 | 89 |
| Control | | 363 ± 51 | |
| | | AV. ± SD. | |
| | | (n = 4) | |

The compounds (I) of the present invention have low toxicity. They do not show any toxic symptoms, when 500 mg/kg of the compounds are orally administered to a mouse.

The compounds (I) of the present invention can be administered orally or parenterally at a daily dose of 0.1 g to 1 g/adult person as an immunosuppressant, and 0.1 g to 10 g/adult person as an antitumor agent in a conventional dosage unit form. For the oral or parenteral administration, they are made up alone or together with a conventional pharmaceutical carrier or diluent to a conventional solid or liquid pharmaceutical preparation, e.g. powders, granules, tablets, capsules, suspensions, emulsions, solutions, using the conventional methods in pharmaceutical field. For example, a tablet or capsule contains 50 to 500 mg of the compounds (I). The compounds (I) of the present invention can be used for an injection, and as drops having water soluble property. The following examples are given to illustrate the present invention more precisely but it is not intended to limit the present invention thereto.

REFERENCE EXAMPLE 1

A mixture of 1.271 g of 4-carbamoylimidazolium-5-olate, 7.263 g of hexamethyldisilazane, 20 ml of dry xylene and 25 mg of anhydrous ammonium sulfate was stirred for two hours under reflux. The clear solution obtained was concentrated in vacuo with protection against moisture to give trimethylsilyl derivative of 4-carbamoylimidazolium-5-olate, which was dissolved in 20 ml of dry 1,2-dichloethane. To the solution was added 0.73 ml of stannic chloride, 1.591 g of 1,2,3,5-tetra-O-acetyl-$\beta$-D-ribofuranose and 91.5 $\mu$l of trimethylsilyl triflate, and the reaction mixture was stirred for two hours under reflux. This mixture was allowed to cool to room temperature and poured into the suspension of 13 g of sodium bicarbonate in 100 ml of methanol. After completeness of neutralization, the mixture was filtered over celite. Evaporation of the filtrate in vacuo gave a residue like carmel, which was extracted with 200 ml of the mixed solvent (40% methanol-1% acetic acid aqueous solution) under heating (70° C., 20 minutes). The mixture was filtered and the filtrate was concentrated in vacuo to give a residue, which was purified by column chromatography on reversed phase silica gel [Merck RP-8 (B-size×2) eluted with aqueous 40% methanol containing acetic acid (1%)] to give 1.520 g (Yield 82.5%) of 4-carbamoyl/1-(2,3,5-tri-O-acetyl-$\beta$-D-ribofuranosyl)imidazolium-5-olate.

Recrystallization from ethanol m.p. 201° C. (dec.)

| Elemental analysis: | C (%) | H (%) | N (%) |
|---|---|---|---|
| Calculated for $C_{15}H_{19}N_3O_9$ | 46.75 | 4.97 | 10.91 |
| Found | 46.38 | 5.00 | 10.79 |

$[\alpha]_D^{23}$ −26.3° (concentration=0.758, in dimethylsulfoxide)

UV spectrum; $\lambda$max 278 nm $\epsilon$13,000, 245 nm $\epsilon$6,300 (in water), $\lambda$max 280 nm $\epsilon$11,400, 244 nm $\epsilon$5,900 (in N-HCl) $\lambda$max 276 nm $\epsilon$14,800 (in N-NaOH)

EXAMPLE 1

To a solution of 30 ml of phosphoryl chloride in 75 ml of dry acetonitrile was added 3.3 ml of water under ice-cooling and the mixture was stirred for one hour at room temperature. After addition of 28.5 ml of dry pyridine to the mixture, further 21 ml of dry acetonitrile was added thereto.

To the solution of dehydrating agent (55 ml) obtained as above was added 11.575 g of 4-carbamoyl-1-(2,3,5-tri-O-acetyl-$\beta$-D-ribofuranosyl)imidazolium-5-olate.

The mixture was stirred for two hours at room temperature and cooled on an ice bath. To the mixture was added 40 ml of cold water. The solution was neutralized by adding sodium bicarbonate thereto. Evaporation of the solution in vacuo gave a residue, which was purified by column chromatography on reversed phase silica gel [Merck RP-8 eluted with aqueous 30% methanol containing acetic acid (1%)] to give 7.137 g of 4-cyano-1-(2,3,5-tri-O-acetyl-$\beta$-D-ribofuranosyl)imidazolium-5-olate.

m.p. 160°–161° C.

FD-Mass m/e; 368 (M+1), 308, 259, 108, 43

$^1$H-NMR$\delta_{DMSO-d6}^{TMS}$ ppm; 8.25 (1H, singlet, imidazole ring proton), 5.70 (1H, doublet, J=5.3 Hz, anomeric proton of sugar)

UV spectrum; $\lambda$max 251 nm $\epsilon$10,200 (in water) $\lambda$max 270 nm $\epsilon$7,400, 233 nm $\epsilon$8,700 (in N-HCl), $\lambda$max 251 nm $\epsilon$12,300 (in N-NaOH)

EXAMPLE 2

To a mixture of 6.921 g of 4-cyano-1-(2,3,5-tri-O-acetyl-$\beta$-D-ribofuranosyl)imidazolium-5-olate and 50 ml of dry methanol was added 20.37 g of 25% (W/W) sodium methoxide methanol solution under ice-cooling. The reaction mixture was stirred for ten minutes at the same temperature and concentrated to dryness in vacuo. The resulting residue was purified by column chromatography on reversed phase silica gel [Merck RP-8 eluted with 1% acetic acid solution] to give 4.21 g of 4-cyano-1-$\beta$-D-ribofuranosylimidazolium-5-olate.

m.p. 148° C. (dec.)

FD-Mass m/e ; 242 (M+1), 223, 133, 109

$^1$H-NMR$\delta_{DMSO-d6}^{TMS}$ ppm; 8.21 (1H singlet, imidazole ring proton), 5.45 (1H, doublet, J=4.8 Hz, anomeric proton of sugar)

UV spectrum; $\lambda$max 254 nm $\epsilon$9,900, 238 nm shoulder (in water), $\lambda$max 267 nm $\epsilon$7,400, 232 nm $\epsilon$8,500 (in N-HCl), $\lambda$max 251 nm $\epsilon$12,900 (in N-NaOH)

EXAMPLE 3

To a mixture of 184 mg of 4-cyano-1-(2,3,5-tri-O-acetyl-$\beta$-D-ribofuranosyl)imidazolium-5-olate and 1 ml of dry methanol was added 15 ml of 15% (W/W) ammonia/methanol solution under cooling, and the mixture was stirred for two hours at the same temperature. Evaporation of the reaction mixture in vacuo gave a residue, which was purified by column chromatography on reversed phase silica gel [Merck RP-8 eluted with aqueous 10% methanol containing acetic acid (1%)] to give 100 mg of 4-cyano-1-(5-O-acetyl-$\beta$-D-ribofuranosyl)imidazolium-5-olate and 32 mg of 4-cyano-1-$\beta$-D-ribofuranosylimidazolium-5-olate, which was identified with the authentic sample of Example 2.

4-cyano-1-(5-O-acetyl-$\beta$-D-ribofuranosyl)imidazolium-5-olate:

m.p. 92° C. (dec.)

FD-Mass m/e; 284 (M+1), 258, 175, 94

$^1$H-NMR$\delta_{DMSO-d6}^{TMS}$ ppm ; 8.16 (1H, singlet, imisazole ring proton), 5.48 (1H, doublet, J=4.2 Hz, anomeric proton of sugar), 2.03(3H, singlet, acetyl methyl)

UV spectrum; $\lambda$max 253 nm $\epsilon$9,700, 238 nm shoulder (in water), $\lambda$max 268 nm $\epsilon$7,100, 232 nm $\epsilon$8,100 (in N-HCl), $\lambda$max 251 nm $\epsilon$12,800 (in N-NaOH)

According to the present invention, there are obtained, for example, the following compounds:

4-Cyano-1-(2,3,5-tri-O-benzoyl-β-D-ribofuranosyl)imidazolium-5-olate

4-Cyano-1-(5-O-benzoyl-β-D-ribofuranosyl)imidazolium-5-olate

We claim:

1. A cyanoimidazole nucleoside of the formula:

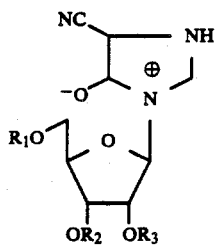

wherein $R_1$, $R_2$ and $R_3$ are each a hydrogen atom or an acyl group and a pharmaceutical salt thereof.

2. A compound according to claim 1 wherein $R_1$, $R_2$ and $R_3$ are each hydrogen.

3. A compound according to claim 1 wherein $R_1$, $R_2$ and $R_3$ are each a hydrogen atom or an acyl group which is an alkanoyl group having 1 to 4 carbon atoms or aroyl.

4. The compound according to claim 1, which is 4-cyano-1-β-D-ribofuranosylimidazolium-5-olate.

5. The compound according to claim 1, which is 4-cyano-1-(2,3,5-tri-O-acetyl-β-D-ribofuranosyl)imidazolium-5-olate.

6. The compound according to claim 1, which is 4-cyano-1-(2,3,5-tri-O-benzoyl-β-D-ribofuranosyl)imidazolium-5-olate.

7. The compound according to claim 1, which is 4-cyano-1-(5-O-acetyl-β-D-ribofuranosyl)imidazolium-5-olate.

8. The compound according to claim 1, which is 4-cyano-1-(5-O-benzoyl-β-D-ribofuranosyl)imidazolium-5-olate.

* * * * *